Figure 1:
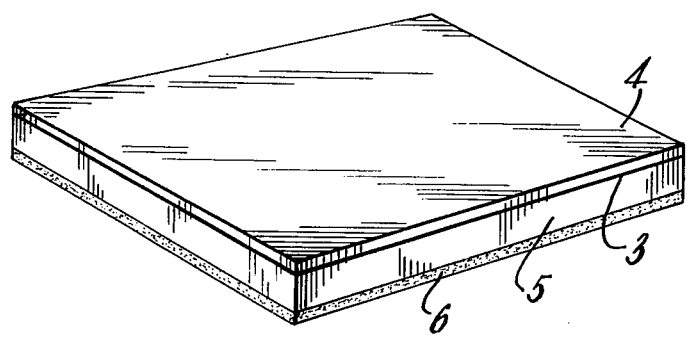

United States Patent [19]

Harwood

[11] 4,230,105
[45] Oct. 28, 1980

[54] TRANSDERMAL DELIVERY OF DRUGS

[75] Inventor: Richard J. Harwood, Philadelphia, Pa.

[73] Assignee: Merck & Co., Inc., Rahway, N.J.

[21] Appl. No.: 960,354

[22] Filed: Nov. 13, 1978

[51] Int. Cl.³ ............................................ A61L 15/00
[52] U.S. Cl. .................................................. 128/156
[58] Field of Search ............................. 128/155–156, 128/260–261, 268, 293, 403

[56] References Cited

U.S. PATENT DOCUMENTS

| 2,573,791 | 11/1951 | Howells | 128/268 |
|---|---|---|---|
| 3,053,255 | 9/1962 | Meyer | 128/268 |
| 3,347,233 | 10/1967 | Migliarese | 128/293 |
| 3,734,097 | 5/1973 | Zaffaroni | 128/268 |
| 3,797,494 | 3/1974 | Zaffaroni | 128/268 |
| 3,929,131 | 12/1975 | Hardwick | 128/403 |
| 3,976,049 | 8/1976 | Yamashita et al. | 128/403 |

Primary Examiner—C. Fred Rosenbaum
Attorney, Agent, or Firm—Thomas E. Arther; Mario A. Monaco; Rudolph J. Anderson, Jr.

[57] ABSTRACT

An improved method for the topical administration of systemically or locally active drugs utilizes a bandage containing one or more layers including a drug useful in the treatment of disease and a heat-generating substance, each dispersed intimately throughout said bandage layers.

2 Claims, 2 Drawing Figures

TRANSDERMAL DELIVERY OF DRUGS

BACKGROUND OF THE INVENTION

This invention relates to an improved method for the topical administration of systemically or locally active drugs. Methods used in the past for such topical or percutaneous delivery of drugs involved incorporating the drug to be administered into a bandage or patch for application to the skin. These bandages, which are employed for topical and/or transdermal drug delivery, consist of multiple layers including a backing layer and a discrete reservoir layer containing a drug confined within a body which is adapted to release a predetermined flow of drug to the skin or mucosa to which it is applied. A pressure-sensitive adhesive surface adapted for contact with the skin or mucosa is positioned on one surface of the reservoir remote from the backing member and may be part of the layer containing the drug reservoir.

Those methods used in the past provide a method of delivering drug to the surface, treated at a predetermined rate, but do not have any substantial effect on the rate of absorption of drug by the surface being treated. Thus, the rate of adsorption of the drug is entirely dependent on the permeability of surface (skin or mucosa) being treated.

DESCRIPTION OF THE INVENTION

In accordance with the present invention, there is provided a method for improving the delivery of drugs when topically administered by application of heat to a drug-containing bandage adapted for transdermal delivery of drugs. Application of heat to the area of bandage containing drug increases the permeability of the membrane with which the drug-containing bandage is in contact, and consequently increases the rate of absorption of drug through the body membrane (skin or mucous membrane).

In accordance with one embodiment of the present invention, there is provided a bandage comprising three discrete layers including (1) a heat-generating area or matrix as one layer separated by a water-impervious layer from (2) a drug-containing matrix or reservoir, and (3) a pressure-sensitive adhesive area for application to the skin or mucous membrane to be treated.

FIG. 1 is a perspective view of the medical adhesive bandage of the invention including a porous matrix containing a heat-generating material dispersed therethrough and separated by a water-impervious film from an intermediate layer of a second porous matrix having a therapeutic drug dispersed evenly throughout the matrix and a pressure-sensitive adhesive area for direct application to the skin of the patient being treated.

Figure 2:
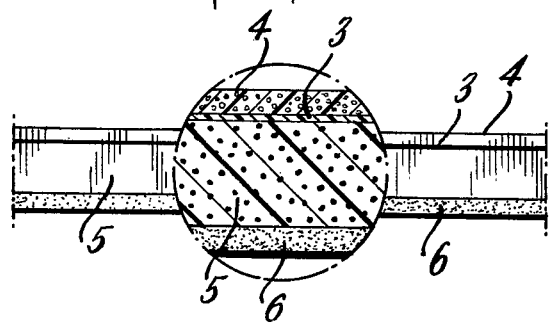

FIG. 2 is a cross-sectional view of the medical adhesive bandage illustrating the same layers described in connection with FIG. 1.

As illustrated in FIGS. 1 and 2 respectively, the heat-generating area or matrix (4) is backed with a water-impervious film (3) which in turn is applied to a drug-containing matrix layer (5) which is in turn coated with a pressure-sensitive adhesive backing material.

In practice, the heat-generating layer (4) can be comprised of a heat-generating chemical intimately dispersed throughout a porous material well known in the art, and includes a plurality of fused polymer particles which provide a supporting structure having therethrough a dispersion of microscopic-sized interconnecting voids and spaces. The heat-generating chemical substance is dispersed evenly throughout the porous matrix and is provided as an anhydrous form of an inorganic hydrate-forming salt which releases heat on taking up water of hydration. Examples of such heat-producing chemicals include anhydrous calcium chloride, sodium sulfate, aluminum chloride, magnesium carbonate, and the like. The heat-producing chemical reaction can be separated from the drug-containing matrix (5) by a thin water-impervious film (3) which permits passage of heat to the drug matrix and the skin of the patient, thereby dilating the pores, increasing the permeability of the skin and consequent absorption of the drug being administered. The drug-containing matrix (5) is conveniently prepared in the manner described in the art, and comprises a unit dosage of drug evenly dispersed through a plurality of fused polymer particles such as is used as the support medium for the heat-generating chemicals. The drug-containing matrix is in intimate contact with the adhesive backing layer (6) which does not substantially impede the passage of the drug from the matrix directly to the surface of the skin. As illustrated in the art, the drug-containing matrix can be either a microporus structure of a hollow reservoir of reservoirs containing solutions or suspensions of the drug being administered.

In addition to the bandage previously described, the bandage may include a heat-generating matrix layer which consists of a non-porous, non-spongelike polymer film; a porous, non-spongelike polymer film; or a porous, spongelike polymer film. Alternatively, when the bandage includes such heat-generating matrices, it is not necessary to include the water-impervious film (3) to prevent intermingling of the drug and heat-generating, hydrate-forming inorganic salt.

In one preferred embodiment, layers 5 and 6—i.e., the drug-containing matrix and the adhesive layer—are coalesced into one, wherein the drug is interspersed intimately throughout the adhesive layer. In such a case, it is preferable to utilize a heat-generating matrix layer which is immiscible with the drug adhesive matrix layer in which case it is not necessary to use the water-impervious film (3) to separate the heat-generating layer from the drug-adhesive layer.

The amount of active agent or drug to be administered to the patient should be in the range of a desirable daily dose of the particular drug being administered, and should be applied to the bandage in the range of 0.25 mg. to about 1 gram/square centimeter of bandage/day. Required daily doses are dependent on the nature of the drug being applied and on the age and weight of the patient for whom the dose is intended.

In carrying out the process of the present invention, any systemically or topically active drug may be used. Suitable systemic drugs include antibiotic agents such as penicillin, cefoxitin, tetracycline, and the sulfonamides; antiinflammatory agents such as dexamethasone, indocin, and sulindac; antihistamines such as cyproheptadine hydrochloride and chlorpheniramine maleate; antidepressant drugs such as amitriptyline and protriptyline; tranquilizer drugs such as chlordiazepoxide, reserpine, promazine, and chlorpromazine; muscle relaxants such as cyclobenzaprine; antifungal agents such as griseofulvin and nystatin; antiviral agents such as idoxuridine useful in the treatment of herpes simplex virus and amantadine hydrochloride useful in the prevention and management of illness caused by influenza A virus strains; antimetabolite agents such as azathioprine and 2-amino-6-mercaptopurine; antivertigo agents such as meclizine chloride; and alkaloids conventionally administered systemically such as scopolamine, tropine, and papaverine, and the like.

Although it will be noted that many of the above-named drugs are usually recommended for systemic use, the drug, when employed as an ingredient of the improved medical adhesive bandage of the present invention, may be administered by the improved transdermal heat-actuated delivery system.

In using the improved medical bandage of the present invention, the bandage is first applied to the area of skin to be treated and is then moistened with sufficient water to effect formation of the inorganic salt hydrate within the heat-generating matrix and produce a local warming effect which enhances absorption of the drug. After moistening the heat-generating area, if desired, an aluminum foil cover may be sealed in place to cover the bandage and prevent loss of heat to the atmosphere.

The following example is merely illustrative of the present invention and is not intended to limit the scope of the invention in any way.

EXAMPLE

Pressure-sensitive adhesive composition is prepared by adding to 100 milliliters of hexane the following:
  20 grams of polyvinylethylether (reduced viscosity = 5.0 ± 0.5)
  4 grams of polyvinylethyl ether (reduced viscosity = 3.0 ± 0.1)
  4 grams of glycerol ester of hydrogenated rosin
  2 grams of polyethylene glycol 400

To the resulting solution are added 10 milligrams of methotrexate, and the solution stirred for 60 minutes.

The resulting methotrexate-containing solution is applied to a 100 by 100 centimeter hydroxypropyl cellulose sheet, which is impregnated with anhydrous calcium chloride, to a uniform thickness and the solvent removed by drying to give about 3 milligrams of adhesive per centimeter square of calcium chloride impregnated hydroxypropyl cellulose sheet. The methotrexate present in the adhesive layer is at a concentration of about 1 microgram per square centimeter. The resulting therapeutic adhesive tape is effective in the treatment of psoriatic lesions when applied directly to the lesions; and the backing material is exposed to a small amount of water. It can be stored for prolonged periods under an inert atmosphere; and is packaged between hermetically sealed, moisture-resistant, aluminum-foil laminated sheets prior to use.

What is claimed is:

1. An improved medical bandage for the administration of drug through the skin or mucosa which comprises a layered bandage comprising first a heat-generating layer containing a hydrate-forming inorganic salt dispersed throughout an inactive matrix layer, and second, a pressure-sensitive adhesive area containing drug to be administered to the patient, dispersed intimately throughout said adhesive layer.

2. An improved medical bandage for the administration of drug through the skin or mucosa which comprises a layered bandage comprising first a heat-generating layer containing a heat-generating chemical substance dispersed throughout an inactive matrix layer, and second, a pressure-sensitive adhesive area containing drug to be administered to the patient, dispersed intimately throughout said adhesive layer.

* * * * *